United States Patent
Ma et al.

(10) Patent No.: US 7,323,296 B2
(45) Date of Patent: Jan. 29, 2008

(54) METHOD AND INDEX FOR DIAGNOSING INSULIN RESISTANCE

(76) Inventors: Yuanhong Ma, 462 Los Ninos Way, Los Altos, CA (US) 94022; Gerald M. Reaven, 180 Tolman Dr., Stanford, CA (US) 94305; Yuanshu Xie, 212 Warren Common, Fremont, CA (US) 94539; Xingyu Wang, Huajiadixili 213-10-501, ChaoYang, Beijing (CN) 100102; Lynn E. Murry, 424 W. Patricia La., Fayetteville, AR (US) 72703

( * ) Notice: Subject to any disclaimer, the term of this patent is extended or adjusted under 35 U.S.C. 154(b) by 0 days.

(21) Appl. No.: 11/240,221

(22) Filed: Sep. 30, 2005

(65) Prior Publication Data

US 2006/0073097 A1    Apr. 6, 2006

Related U.S. Application Data

(60) Provisional application No. 60/615,280, filed on Oct. 1, 2004.

(51) Int. Cl.
*A01N 1/02* (2006.01)
*G01N 33/48* (2006.01)

(52) U.S. Cl. .............................. 435/2; 436/63

(58) Field of Classification Search ..................... None
See application file for complete search history.

(56) References Cited

OTHER PUBLICATIONS

Brehm et al. Relationship Between Serum Lipoprotein Ratios and Insulin Resistance in Obesity; Clinical Chemistry, vol. 50, No. 12 (2004) pp. 2316-2322.*
Zavaroni et al. Plasma Nitric Oxide Concentrations are Elevated in Insulin-Resistant Healthy Subjects; Metabolism, vol. 49, No. 8 (2000) pp. 959-961.*
Abbasi F et al. (2002) Relationship between obesity, inuslin resistance, and coronary heart disease risk. J Amer College Cardiol 40:937-43.

ADA (2002) The prevention or delay of type 2 diabetes. Diabetes Care 25:742-49.
ADA (2003) Economic costs of diabetes in the US in 2002. Diabetes Care 26:917-32.
Facchini F et al. (2001) Insulin resistance as a predictor of age-related diseases. J Clin Endocrin Metabol 86:3574-78.
Hrebicek J et al. (2002) Detection of insulin resistance by simple quantitative insulin check index . . . J Clin Endocrinol Met 87:144-47.
McLaughlin T et al. (2003) Use of Metabolic Markers To Identify Overweight Individuals Who Are Insulin Resistant Ann Intern Med. 139:802-9.
Matsuda M and RA DeFronzo (1999) Insulin Sensitivity Indices Obtained from Oral Glucose Tolerance Testing. Diabetes Care 22:1462-70.
Matthews DR et al.(1985) Homeostasis model assessment: insulin resistance and beta-cell function . . . Diabetologia 28:412-9 (abstract only).
Nyholm B et al. (2004) Evidence of increased visceral obesity and reduced physical fitness in healthy insulin-resistant first-degree relatives . . . Eur J Endocrinol 150:207-214.
Reaven GM et al. 2004. Obesity, Insulin Resistance, and Cardiovascular Disease Recent Prog Horm Res. 59:207-23 (abstract only).

* cited by examiner

*Primary Examiner*—Jon Weber
*Assistant Examiner*—Paul Martin
(74) *Attorney, Agent, or Firm*—Lindera LLC; Lynn E. Murry

(57) ABSTRACT

The invention provides a method for the determination of insulin sensitivity, insulin resistance, and non-insulin dependent Diabetes mellitus based on oral glucose tolerance test data and lipid ratios from reference populations that define an insulin resistance index. The invention also provides methods for using the IR index to determine disease progression and to evaluate the efficacy of the therapeutic agents. The invention further provides an IR calculator for automating diagnosis, producing and storing patient medical records.

14 Claims, 5 Drawing Sheets

| Gender | Age | OGTT Glucose | | | OGTT Insulin | | | TG | HDL | TG/HDL Ratio |
|---|---|---|---|---|---|---|---|---|---|---|
| | | 0' | 60' | 120' | 0' | 60' | 120' | | | |
| M | 33 | 95 | 91 | 74 | 4 | 15 | 3 | 59 | 57 | 1.0 |
| F | 52 | 97 | 93 | 85 | 1 | 16 | 5 | 58 | 58 | 1.0 |
| F | 32 | 70 | 116 | 81 | | 48 | 27 | 38 | 60 | 0.6 |
| F | 48 | 98 | 95 | 89 | 6 | 30 | 22 | 88 | 77 | 1.1 |
| F | 36 | 86 | 80 | 68 | 6 | 42 | 21 | 49 | 65 | 0.8 |
| F | 35 | 94 | 86 | 80 | 13 | 62 | 28 | 69 | 58 | 1.2 |
| M | 47 | 93 | 99 | 59 | 10 | 56 | 13 | 84 | 66 | 1.3 |
| M | 58 | 91 | 87 | 84 | 13 | 49 | 15 | 91 | 47 | 1.9 |
| F | 34 | 79 | 78 | 88 | 11 | 23 | 36 | 53 | 56 | 1.0 |
| F | 38 | 90 | 87 | 98 | 7 | 32 | 31 | 92 | 71 | 1.3 |
| F | 35 | 84 | 99 | 97 | 7 | 50 | 39 | 55 | 75 | 0.7 |
| M | 44 | 99 | 97 | 98 | 4 | 17 | 17 | 45 | 59 | 0.8 |
| F | 57 | 73 | 99 | 87 | 4 | 43 | 35 | 83 | 73 | 1.1 |
| F | 34 | 92 | 102 | 75 | 8 | 45 | 17 | 68 | 36 | 1.9 |
| F | 38 | 83 | 62 | 57 | 3 | 28 | 6 | 49 | 68 | 0.7 |
| F | 50 | 95 | 94 | 90 | 3 | 31 | 21 | 53 | 79 | 0.7 |
| F | 48 | 88 | 102 | 89 | 8 | 25 | 25 | 92 | 66 | 1.4 |
| F | 52 | 84 | 120 | 90 | 7 | 27 | 17 | 50 | 87 | 0.6 |
| M | 49 | 81 | 100 | 94 | 5 | 33 | 22 | 59 | 64 | 0.9 |
| M | 51 | 91 | 99 | 74 | 8 | 34 | 27 | 117 | 59 | 2.0 |
| M | 53 | 111 | 102 | 82 | 9 | 36 | 11 | 59 | 48 | 1.2 |
| F | 50 | 87 | 107 | 96 | 12 | 49 | 24 | 97 | 84 | 1.2 |
| F | 43 | 93 | 117 | 81 | 12 | 57 | 35 | 97 | 58 | 1.7 |
| F | 43 | 85 | 108 | 75 | 3 | 47 | 21 | 56 | 90 | 0.6 |
| F | 41 | 82 | 112 | 83 | 4 | 50 | 26 | 93 | 54 | 1.7 |
| F | 47 | 86 | 116 | 88 | 6 | 35 | 16 | 84 | 63 | 1.3 |
| F | 52 | 91 | 114 | 92 | 8 | 43 | 24 | 64 | 69 | 0.9 |
| F | 41 | 92 | 101 | 68 | 4 | 38 | 28 | 44 | 56 | 0.8 |
| M | 45 | 79 | 90 | 67 | 19 | 78 | 39 | 104 | 63 | 1.7 |
| F | 48 | 85 | 114 | 83 | 5 | 49 | 37 | 78 | 58 | 1.3 |
| F | 38 | 77 | 100 | 75 | 9 | 49 | 33 | 77 | 68 | 1.1 |
| M | 41 | 91 | 104 | 88 | 11 | 53 | 35 | 40 | 63 | 0.6 |
| M | 41 | 74 | 111 | 76 | 6 | 51 | 22 | 71 | 73 | 1.0 |
| F | 49 | 92 | 106 | 92 | 2 | 32 | 23 | 94 | 76 | 1.2 |
| F | 52 | 83 | 95 | 79 | 2 | 31 | 8 | 62 | 69 | 0.9 |
| F | 35 | 85 | 97 | 77 | 3 | 48 | 23 | 40 | 64 | 0.6 |
| F | 48 | 96 | 80 | 81 | 7 | 31 | 18 | 95 | 53 | 1.8 |
| F | 40 | 81 | 93 | 86 | 4 | 33 | 31 | 95 | 69 | 1.4 |
| M | 36 | 84 | 117 | 97 | 5 | 55 | 31 | 114 | 78 | 1.5 |
| F | 31 | 81 | 104 | 91 | 4 | 46 | 19 | 94 | 92 | 1.0 |
| F | 40 | 104 | 108 | 96 | 19 | 41 | 29 | 49 | 66 | 0.7 |

FIGURE 1

| Gender | Age | OGTT Glucose | | | OGTT Insulin | | | TG | HDL | TG/HDL Ratio |
|---|---|---|---|---|---|---|---|---|---|---|
| | | 0' | 60' | 120' | 0' | 60' | 120' | | | |
| F | 54 | 91 | 180 | 140 | 28 | 125 | 148 | 209 | 40 | 5.2 |
| M | 39 | 106 | 252 | 198 | 5 | 80 | 210 | 454 | 38 | 12.0 |
| F | 48 | 104 | 208 | 139 | 15 | 101 | 100 | 78 | 50 | 1.6 |
| M | 52 | 98 | 210 | 171 | 10 | 85 | 139 | 99 | 35 | 2.8 |
| M | 50 | 124 | 219 | 139 | 14 | 76 | 66 | 89 | 55 | 1.6 |
| F | 42 | 91 | 215 | 173 | 16 | 107 | 121 | 258 | 45 | 5.7 |
| M | 53 | 103 | 200 | 131 | 24 | 192 | 149 | 571 | 34 | 16.8 |
| F | 50 | 102 | 214 | 136 | 20 | 72 | 65 | 212 | 46 | 4.6 |
| F | 45 | 95 | 179 | 174 | 14 | 66 | 101 | 86 | 65 | 1.3 |
| F | 53 | 105 | 208 | 169 | 7 | 66 | 87 | 174 | 57 | 3.1 |
| M | 48 | 102 | 182 | 139 | 18 | 87 | 69 | 580 | 46 | 12.6 |
| F | 64 | 107 | 181 | 186 | 16 | 107 | 136 | 107 | 77 | 1.4 |
| M | 38 | 111 | 243 | 196 | 14 | 84 | 97 | 197 | 46 | 4.3 |
| F | 50 | 105 | 171 | 186 | 9 | 105 | 88 | 136 | 49 | 2.8 |
| M | 58 | 91 | 226 | 154 | 11 | 64 | 63 | 222 | 34 | 6.5 |
| M | 55 | 93 | 181 | 159 | 9 | 134 | 101 | 177 | 46 | 3.9 |
| F | 54 | 81 | 173 | 136 | 9 | 77 | 84 | 202 | 46 | 4.4 |
| M | 36 | 90 | 227 | 191 | 19 | 79 | 87 | 141 | 44 | 3.2 |
| F | 41 | 97 | 185 | 151 | 12 | 67 | 98 | 97 | 67 | 1.5 |
| F | 51 | 105 | 180 | 148 | 34 | 158 | 161 | 323 | 57 | 5.7 |
| M | 31 | 98 | 246 | 151 | 10 | 77 | 62 | 245 | 40 | 6.1 |
| F | 50 | 88 | 175 | 165 | 18 | 154 | 240 | 220 | 40 | 5.5 |
| F | 47 | 93 | 179 | 146 | 19 | 67 | 85 | 138 | 63 | 2.2 |
| F | 50 | 95 | 198 | 139 | 32 | 159 | 113 | 101 | 57 | 1.8 |
| M | 33 | 89 | 197 | 166 | 21 | 132 | 212 | 369 | 33 | 11.2 |
| M | 39 | 97 | 182 | 129 | 20 | 93 | 76 | 166 | 41 | 4.1 |
| M | 52 | 84 | 201 | 197 | 15 | 95 | 119 | 373 | 69 | 5.4 |
| F | 51 | 88 | 182 | 132 | 17 | 71 | 90 | 168 | 65 | 2.6 |
| F | 47 | 90 | 261 | 196 | 35 | 194 | 179 | 133 | 76 | 1.8 |
| M | 51 | 121 | 283 | 147 | 22 | 240 | 91 | 146 | 59 | 2.5 |
| M | 51 | 99 | 206 | 148 | 9 | 111 | 81 | 102 | 45 | 2.3 |
| M | 39 | 112 | 257 | 142 | 27 | 107 | 76 | 373 | 35 | 10.7 |
| M | 41 | 123 | 275 | 185 | 15 | 104 | 83 | 274 | 44 | 6.2 |
| M | 42 | 98 | 272 | 140 | 17 | 111 | 86 | 155 | 60 | 2.6 |
| F | 59 | 116 | 201 | 186 | 22 | 109 | 145 | 108 | 51 | 2.1 |
| F | 35 | 96 | 200 | 141 | 13 | 87 | 111 | 83 | 47 | 1.8 |
| M | 31 | 87 | 221 | 141 | 11 | 149 | 91 | 149 | 37 | 4.0 |
| M | 50 | 108 | 219 | 146 | 23 | 240 | 186 | 200 | 40 | 5.0 |
| F | 63 | 99 | 172 | 141 | 9 | 137 | 76 | 188 | 39 | 4.8 |

Insulin Resistance Calculator

Record  Help

Enter Test Result Below:

OGTT Glucose
- 0 min    [92]    mg/dl
- 60 min   [247]   mg/dl
- 120 min  [150]   mg/dl OGTT Insulin
- 0 min    [9.21]  μ IU/ml
- 60 min   [82.97] μ IU/ml
- 120 min  [57.3]  μ IU/ml Other
- TG   [110]  (mg/dl)
- HDL  [40]   (mg/dl)

ALT  [45]  (U/L)

New Record      Cancel    Back <<    Calculate >>

FIGURE 3 B

IR Calculator Report

Record  Help

IS or IR Status

IR Result

You have been diagnosed as IR. This test of your ability to metabolize glucose has shown that you are at risk of developing type 2 diabetes and IR-related conditions. Please consult your doctor or clinic about the best treatment for you. You can affect disease progression by beginning a regular exercise program, following a healthy diet as recommended by the ADA, AHA, the clinic or your physician, and/or by taking certain medicines to reduce risk factors such as high blood pressure, cholesterol and obesity.
Please re-test OGTT about once a year.

[Save Record >]  [Back <]  [Exit]

IS and IR Standards

| Test | Min | IS | IR | NIDDM |
|---|---|---|---|---|
| OGTT glucose (mg/dl) | 0 | <126 | <126 | ≥126 |
| " | 60 | ≤121 | ≥170 | |
| " | 120 | ≤100 | ≥127 and ≤199 | ≥200 |
| OGTT insulin (μIU/ml) | 0 | ≤24 | ≤55 | |
| " | 60 | <50 | >60 | |
| " | 120 | <40 | >60 | |
| TG/HDL Ratio | | <2 | | |

Database Records for Medical Record Number  00121

| Date | ALT | TG/HDL | Glucose 0' | Glucose 60' | Glucose 120' | Insulin 0' | Ins |
|---|---|---|---|---|---|---|---|
| 2002-8-31 | 22 | 2.22 | 117 | 234 | 189 | 11.2 | 53 |
| 2003-8-31 | 33 | 2.86 | 107 | 220 | 216 | 40.71 | 18 |
| ▶ 2004-8-31 | 45 | 2.75 | 92 | 247 | 150 | 9.21 | 82 |

FIGURE 3 C

METHOD AND INDEX FOR DIAGNOSING INSULIN RESISTANCE

FIELD OF THE INVENTION

The invention comprises methods and an insulin resistance index for diagnosing insulin resistance.

BACKGROUND

Insulin resistance (IR) is a condition in which cells and tissues have a decreased sensitivity to insulin, and secretion of insulin is increased to compensate for impaired glucose metabolism. The ability of insulin to stimulate glucose disposal has been reported to vary more than six-fold in apparently healthy individuals (Reaven et al. (2004) Recent Prog Horm Res 59:207-23), and it is well known that first-degree relatives of type 2 diabetics are often IR (Nyholm et al. (2004) Eur J Endocrinol 150:207-214). Individuals diagnosed as IR may show symptoms of IR syndrome also known as metabolic syndrome and syndrome X (Reaven GM (1988) Diabetes 37:1595-1607), and are at increased risk for developing non-insulin dependent Diabetes mellitus (NIDDM).

Two procedures that have been used to detect IR are euglycemic insulin clamp technique (EIC; Andres et al. In: Skeggs LT (1966) Automation in Analytical Chemistry. pp 486-491) and steady-state plasma glucose (SSPG) test (Greenfield MS (1982) Diabetes 30:387-392). Both methods monitor insulin-mediated glucose disposal in vivo and are considered to be the "gold-standard" for detection of IR. Both of these procedures are cumbersome in that they require hospitalization, multiple infusions using a catheter, and sampling over time. The limitations of EIC include the inability to reproduce physiological conditions, use of more than one dose of insulin to achieve a steady state glucose level, test complexity that precludes use in a clinical setting and, ultimately, cost.

Other methods for estimating IR include the minimal model (MM), an intravenous glucose tolerance test (Bergman et al. (1987) J Clin Invest 79:790-800), homeostasis model assessment (HOMA-IR; Matthews et al.(1985) Diabetologia 28:412-419) and quantitive insulin check index (QUICKI; Hrebicek et al. (2002) J Clin Endocrinol Metab 87:144-1470). HOMA-IR calculations are based on fasting glucose and insulin measurements [R=insulin (mU/L)/22.5e$^{-ln\ glucose(mmol/liter)}$ or R=(insulin×glucose)/22.5) in simplified form]. QUICKI can be determined from fasting insulin and glucose values according to the equation. QUICKI=1/[log (I0)+log (G0)], in which I0 is fasting insulin and G0 is fasting glucose. There are also limitations for each of these methods, MM has variable accuracy in diabetics whose immediate plasma insulin response is already diminish, and HOMA-IR and QUICKI are indirect e s for IR that rely heavily on the fasting plasma glucose and insulin measurement which correlate poorly with EIC or SSPG data (Tuan C Y et al. (2003) Am J Cardiol 92:606-610).

Matsuda and DeFronzo (1999 D Care 22:1462-1477) Resented a method for evaluaating insulin sensitivity (IS) based on euglycemic insulin clamp studies. Although the authors developed a formula for calculating whole body IS correlated with oral glucose tolerance test (OGTT), the method was not reduced to or presented in a format easily adapted for clinical screening.

In a recent study, Facchini et al. (2001; J Clin Endocrin Metabol 86:3574-78) showed a strong correlation between the ability to use insulin in glucose metabolism and the onset of age-related diseases. Some 208 healthy, non-obese volunteers over 30 years of age were chosen for this SSPG study on the basis of body mass index less than 30, lack of hypertension, blood pressure less than 140/90 mm Hg, normal OGTT, physical examination and clinical chemistries Over a period of 4-11 years, volunteers were evaluated for development of age-related diseases. The most notable result from this study was that the most insulin sensitive volunteers had zero incidence of age-related diseases such as cancer, coronary heart disease, hypertension, NIDDM, and stroke. The authors stated a need for distinguishing subjects who were IS from those who were IR in order to monitor the development of age-related diseases in the IR group.

Because overweight individuals can be either IR or IS, McLaughlin et al. (2003, Annals of Internal Medicine 139: 802-809) evaluated boy mass index; fasting glucose, SSPG, insulin, and lipid concentrations for the ability to identify the subset of overweight individuals who are IR. They reported that a triglyceride/high density lipoprotein cholesterol ratio (TG/HDL) is useful in identifying IR subjects.

IR and NIDDM have a strong genetic component (Abbasi et al. (2002) J Amer College Cardiol 40:937-43); so the ability to accurately identify susceptible individuals is of great importance. Adults with IR have up to 10 times greater risk of death from cardiovascular disease and are at greater risk for NIDDM—the leading cause of damage to or failure of eyes, kidneys and nerves According the World Health Organization, NIDDM is now the most costly healthcare issue worldwide.

Once there is an IR diagnosis, the subject can be counseled to modify diet, begin an exercise program, lose weight and take drugs to improve insulin sensitivity and delay onset of IR-related conditions and conversion to NIDDM (American Diabetes Association (ADA) 2002; Diabetes Care 25:742-49). The benefit of reducing healthcare costs associated with early diagnosis of IR, NIDDM and IR- or age-related diseases is well documented by the ADA (2003; Diabetes Care 26:917-32) and American Heart Association (AHA).

There is a need in the art for a more practical and cost-effective method for screening and diagnosing IS and IR. The earlier that subjects can be diagnosed as IS or IR, the greater the savings in terms of personal, medical and societal costs.

SUMMARY

The invention presents a method for diagnosing whether a subject is insulin sensitive (IS), insulin resistant (IR) or diabetic (NIDDM) comprising f 75 grams of glucose to the subject; obtaining samples from the subject at 0, 60 and 120 min after glucose administration; performing tests on the samples to obtain sample readings wherein the sample readings are concentrations of glucose, insulin, triglyceride (TG) and high density lipoprotein (HDL); calculating TG/HDL ratio from the sample readings for TG and HDL; and comparing sample readings for glucose and insulin concentration and TG/HDL ratio to readings from reference populations wherein a first reference population that has been diagnosed as insulin sensitive has a glucose concentration at 0 min that is less than 126 mg/dl, at 60 min that is less than or equal to 121 mg/dl and at 120 min is less than or equal to 100 mg/dl; an insulin concentration at 0 min that is less than or equal to 19 µIU/ml, at 60 min that is less than 50 µIU/ml and at 120 min that is less than 40 µIU/ml; and a TG/HDL ratio that is less than 2; a second reference population that has been diagnosed as insulin resistant has a glucose concentration at 0 min that is less than 126 mg/dl, at 60 min that is equal to or greater than 170 mg/dl and at 120 min is less than or equal to or greater than 127 and less than 200 mg/dl and an insulin concentration at 0 min that is less than or equal to 55 μIU/ml and at 60 min or at 120 min that is greater than 60 μIU/ml; and a third reference population that has been diagnosed as NIDDM has a glucose concentration at 0 min that is equal to or greater than 126 mg/dl or at 120 min that is greater than 200 mg/dl; and diagnosing whether the subject is insulin sensitive, IR or NIDDM based on the comparison.

The invention also presents a method for diagnosing whether a subject is insulin sensitive (IS), insulin resistant (IR) or diabetic (NIDDM) comprising administering 75 grams of glucose to the subject; obtaining samples from the subject at 0, 60 and 120 min after glucose administration; performing tests on the samples to obtain sample readings wherein the sample readings are concentrations of glucose, insulin, TG and HDL; calculating TG/HDL ratio from the sample readings for TG and HDL; and comparing sample readings for glucose and insulin concentrations and TG/HDL ratio to an IR index wherein the IR index has endpoints derived from sample readings of a first reference population that has been diagnosed as insulin sensitive and has a glucose concentration at 0 min that is less than 126 mg/dl, at 60 min that is less than or equal to 121 mg/dl and at 120 min is less than or equal to 100 mg/dl; an insulin concentration at 0 min that is less than or equal to 19 μIU/ml, at 60 min that is less than 50 μIU/ml or at 120 min that is less than 40 μIU/ml; and a TG/HDL ratio that is less than 2; a second reference population that has been diagnosed as insulin resistant and has a glucose concentration at 0 min that is less than 126 mg/dl, at 60 min that is equal to or greater than 170 mg/dl and at 120 min that is equal to or greater than 127 and less than 200 mg/dl and an insulin concentration at 0 min that is less than or equal to 55 μIU/ml and at 60 min or at 120 min that is greater than 60 μIU/ml; and a third reference population that has been diagnosed as NIDDM and has a glucose concentration at 0 min that is equal to or greater than 126 mg/dl and at 120 min that is greater than 200 mg/dl; and diagnosing whether the subject is insulin sensitive, IR or NIDDM based on the comparison.

The invention further presents a method wherein the ranges for glucose and insulin concentrations and TG/HDL ratio in reference populations define an insulin resistance index (IR index) further comprising a diagnosis of IS if a subject has a glucose concentration at 0 min that is from about 50 mg/dl to about 125 mg/dl, at 60 min that is from about 62 mg/dl to about 121 mg/dl and at 120 min that is from about 57 mg/dl to about 100 mg/dl; an insulin concentration at 0 min that is flow about 1 μIU/ml to about 24 μIU/ml and at 60 min that is from about 17 μIU/ml to about 50 μIU/ml or at 120 min that is from about 3 μIU/ml to about 40 μIU/ml; and a TG/HDL ratio that is less than 2; a diagnosis of IR if a subject has a glucose concentration at 0 min from about 81 mg/dl to about 125 mg/dl, at 60 min from about 170 mg/dl to about 283 mg/dl, and at 120 min that is from about 127 to about 199 mg/dl; an insulin concentration at 0 min that is from about 4 μIU/ml to about 55 μIU/ml and at 60 min or at 120 mm that is from about 60 μIU/in to about 240 μIU/ml; and a diagnosis of NIDDM if a subject has a glucose concentration at 0 min that is greater than 126 mg/dl or at 120, that is greater than 200 mg/dl.

The invention still further presents a method for diagnosing whether a subject is insulin sensitive (IS), insulin resistant (IR) or diabetic (NIDDM) comprising administering 75 grams of glucose to the subject; obtaining samples from the subject at 0, 60 and 120 min after glucose administration; performing tests on the samples to obtain sample readings wherein the sample reads are concentrations of glucose, insulin, TG and HDL; calculating TG/HDL ratio from the sample reading for TG and HDL; and comparing sample readings for glucose and insulin concentrations and TG/HDL ratio to an IR index wherein the comparison provides a diagnosis of IS if a subject has a glucose concentration at 0 min that is from about 50 mg/dl to about 125 mg/dl, at 60 min that is from about 62 mg/dl to about 121 mg/dl, and at 120 min that is from about 57 mg/dl to about 100 mg/dl; an insulin concentration at 0 min that is from about 1 μIU/ml to about 24 μIU/ml and at 60 min that is from about 17 μIU/ml to about 50 μIU/ml or at 120 min that is from about 3 μIU/ml to about 40 μIU/ml; and a TG/HDL ratio that is less than 2; a diagnosis of IR if a subject has a glucose concentration at 0 min from about 81 mg/dl to about 125 mg/dl, at 60 min from about 170 mg/dl to, about 283 mg/dl, and at 120 min that is from about 127 to about 199 mg/dl; an insulin concentration at 0 min that is from about 4 μIU/ml to about 55 μIU/ml and at 60 min or at 120 min that is from about 60 μIU/ml to about 240 μIU/ml; and a diagnosis of NIDDM if a subject has a glucose concentration at 0 min that is greater than 126 mg/dl or at 120 that is greater than200 mg/dl.

The invention yet still further presents a method wherein a subject is screened to determine IS, IR or NIDDM status comprising administrating 75 grams of glucose to the subject; obtaining samples from the subject at 0, 60 and 120 min after glucose administration; performing tests on the samples to obtain sample readings wherein the sample readings are concentrations of glucose, insulin, TG and HDL; calculating TG/HDL ratio from the sample readings for TG and HDL; and cm i ring sample readings for glucose and insulin concentrations and TG/HDL ratio to the IR index, thereby determining whether the subject is IS, IR or NIDDM.

The invention presents a method wherein a diagnosis of IR is prognostic of IR-related conditions. and wherein IR-related conditions are selected from dyslipidemia, hypoglycemia hyerperinsulinemiailia, metabolic syndrome, nonalcoholic fatty liver disease obesity, polycystic ovary syndrome, prediabetes, sleep apnea, syndrome x; cardiovascular diseases such as atherosclerosis peripheral vascular disease, essential hypertension, myocardial infarction and stoke; and cancers such as breast, colorectal and prostate cancer. The invention also presents a method wherein a diagnosis of IS or IR suggests a frequency for retesting. The invention further presents a method of wherein the b for resting for an IS subject is about once every three years. The invention further presents a method wherein the frequency for retesting for a subject who is IR is about once a year. The invention still further presents a method wherein a previously diagnosed IS subject is e d further comprising administering 75 grams of glucose to the subject; obtaining samples from the subject at 0, 60 and 120 min after glucose, administration; performing tests on the samples to obtain sample readings wherein the sample readings are concentrations of glucose, insulin, TG and HDL; calculating TG/HDL ratio from the sample readings for TG and HDL; and comparing sample readings for glucose and insulin concentrations and TG/HDL ratio to the IR index; and diagnosing whether the subject is IS, IR or NIDDM based on the comparison. The invention yet still further presents a method wherein subject previously diagnosed as IR is retested further comprising administering 75 grams of glucose to the subject; obtaining samples from the subject at 0, 60 and 120 min after glucose administration; performing tests on the samples to obtain sample readings wherein the sample readings are concentrations of glucose, insulin, TG and HDL; calculating TG/HDL ratio from the sample readings for TG and HDL; and comparing sample readings for glucose and insulin concentration and TG/HDL ratio to the IR index; and diagnosing whether the subject is IS, IR or NIDDM based on the comparison. The invention additionally presents a method wherein a subject previously diagnosed as IR is evaluated for disease progression further comprising administering 75 grams of glucose to the subject; obtaining samples from the subject at 0, 60 and 120 min after glucose administration; performing tests on the samples to obtain sample readings wherein the sample readings are concentrations of glucose, insulin, TG and HDL; calculating TG/HDL ratio from the sample readings for TG and HDL; and comparing sample readings for glucose and insulin concentration and TG/HDL ratio to the IR index; and detaining that increased sample reading concentrations causing a change in status from IS to IR or from IR to NIDDM indicates disease progression.

The invention presents a method for comparing sample readings to the IR index using an IR calculator. The invention also presents a method wherein the IR calculator is loaded into a programmable device or is accessible on the world-wide-web. The invention further presents a method wherein the IR calculator is used to automate comparisons in batch mode. The invention still further presents a method wherein the IR calculator is used to generate a patient record containing medical record number, name, address, date of birth, gender, date of test, glucose concentrations, insulin concentrations, TG/HDL ratio, ALT, IS, IR or NIDDM status, standard ranges defining IS, IR, and NIDDM, and frequency for retesting. The invention yet still further presents a method wherein any previous sample readings for a patient found in a database are listed by date in the patient's record.

The invention additionally presents a method wherein determination of IR or NIDDM status suggests lifestyle change and/or medical intervention.

The invention presents a method for determining efficacy of a agent for treating IR or NIDDM comprising treating a subject diagnosed as IR or NIDDM with an agent; administering 75 grams of glucose to the subject; obtaining samples from the subject at 0, 60 and 120 min after glucose administration; performing tests on the samples to obtain sample readings wherein the sample readings are concentrations of glucose, insulin, TG and HDL; calculating TG/HDL ratio from the sample readings for TG and HDL; comparing sample readings for glucose and insulin concentration and TG/HDL ratio to the IR index; and determining that decreased readings after treatment indicates efficacy. The invention also a method wherein an agent is selected firm agonists for cholecystokinin alpha melanocyte stimulating hormone, stearoyl-CoA desaturase-1; antibodies, antagonists or inhibitors for agouti-related peptide, AMP-activated protein kinase, ghrelin, leptin, neuropeptide Y, protein tyrosine phosphatase 1B, and resistin; antihyperglycemic agents such as the alpha glucosidase inhibitor acarbose or the starch blocker miglitol; biguanides, chromium, dissaccharide inhiubitors; insulin sensitizers such as avandamet, D-phenylalanine derivative nateglinide, halofenate or its derivatives, metformin, meglitinides, pioglitazne, repaglinide, rosiglitazone, troglitazone and thiazolidenedione compounds; a peroxisome proliferator-activated receptor agonist; proteins such as adiponectin and ciliary neutrophic factor, rimonabant; succinic acid or a salt thereof, sulfonylurea compounds such as acetohexamide, chlorpropamide, glimepiride, glipizide, glyburide, tolazamide, and tolbutamide.

DESCRIPTION OF THE FIGURES

FIG. 1 Exemplary data showing OGTT, TG and HDL test results from the Beijing IS reference population used in defining the IR index.

FIG. 2. Exemplary data showing OGTT, TG and HDL test results from Beijing IR reference population used in defining the IR index.

FIGS. 3A, 3B and 3C. Screenshots showing the IR calculator and report.

DETAILED DESCRIPTION OF THE INVENTION

It is understood that this invention is not limited to the particular machines, materials and methods described. It is also to be understood that the terminology is used for the purpose of describing particular embodiments and is not intended to limit the scope of the invention which will be limited only by the claims. The singular forms "a", "an" and "the" may include plural reference unless context clearly dictates otherwise. For example, a reference to "a device" includes a plurality of such devices known to those skilled in the art.

Unless defined otherwise, all technical and scientific terms have the same meanings as commonly understood by one of ordinary skill in the art to which this invention belongs. All publications are cited for the purpose of describing and disclosing protocols, reagents and machinery which might be used in connection with the invention. Nothing in this patent is to be construed as an admission that the invention is not entitled to antedate such disclosure by virtue of prior invention.

DEFINITIONS

"Agent" refers to any therapeutic molecule or compound that either increases insulin sensitivity or reduces IR, can be used either to delay or treat IR, IR-related conditions, NIDDM or NIDDM-associated conditions and can be selected from agonists for cholecystokinin, alpha melanot stimulating hormone, stearoyl-CoA desaturase-1; antibodies, antagonists or inhibitors for agouti-related peptide, AMP-activated protein kinase, ghrelin, leptin, neuropeptide Y, protein tyrosine phosphatase 1B, and resistin; antihyperglycemic agents such as the alpha glucosidase inhibitor acarbose or the starch blocker miglitol; biguanides, chromium, dissaccharide inhibitors; insulin sensitizers such as avandamet, nateglinide, halofenate or its derivatives, metformin, meglitinides, pioglitazne, repaglinide, rosiglitazone, troglitazone and thiazolidenedione compounds; a peroxisome proliferator-activated receptor agonist; proteins such as adiponectin and ciliary neutrophic factor; rimonabant; succinic acid or a salt thereof, sulfonylurea compounds such as acetohexamide, chlorpropamide, glimepiride, glipizide, glyburide, tolazamide, tolbutamide and the like.

"Device" refers to a programmable scientific calculator; a CD; the hard drive, memory, or central processing unit of a compute; a personal data assistant; a cell phone with fold-out or virtual keyboards, and the like.

"Insulin sensitive" or "Insulin sensitivity" (IS) is the ability to produce and utilize insulin to metabolize glucose.

"Insulin resistance" or "Insulin resistant" (IR) is the decreased ability to produce and utilize insulin to metabolize glucose.

"IR-related conditions" are pre-diabetic conditions, diseases, or disorders that include dyslipidemia, hypoglycemia, hyperinsulinemia, metabolic syndrome, nonalcoholic fatty liver disease, obesity, polycystic ovary syndrome, prediabetes, sleep apnea, syndrome x; cardiovascular diseases such as atherosclerosis, peripheral vascular disease, essential hypertension, myocardial infarction and stroke; and cancers such as breast, colorectal and prostate cancer.

"Lifestyle changes" refer to change in diet and exercise such as those suggested by the ADA or AHA that can delay the onset or ameliorate the symptoms of IR, IR-related conditions, NIDDM and NIDDM-associated conditions.

"Medical intervention" refers to the use of agents or drugs prescribed by a medical practitioner to control IR, IR-related conditions, NIDDM and NIDDM associated conditions.

"NIDDM" (No-insulin dependent Diabetes mellitus or type 2 diabetes) is characterized by hypoglycemia, occurring from a decrease in IS and/or an increase in IR, and the failure of increased insulin secretion to compensate for the impaired glucose metabolism and associated with serious vascular, renal, and neurological complications that can cause premature death if undiagnosed untreated.

"NIDDM-associated conditions" include all IR-related conditions, degenerative joint disease, neurological diseases and disorders such as neuralgia, neropathy, ischemic and hemorrhagic stroke, transit ischemic attacks and cerebrovascular disease; peripheral vascular diseases such as atherosclerosis, gangrene, thrombosis, and chronic diabetic foot ulcers; cardiovascular diseases such as aneurysms, angina, cardiac dysrhythmias, cardiomyopathy, hypertension, hypotension, ischemic heart disease and myocardial infarction; renal disease such as nephropathy, proteinuria, and renal failure; endocrine/metabolic complications, opthalmic complications including cataract, glaucoma, and blindness; and compromised response to bacterial and fungal infections.

"OGTT" (oral glucose tolerance test) refers to a standard test used to determine a subject's ability to produce and utilize insulin to metabolize glucose based on plasma glucose or insulin concentrations in a sample at specified time intervals after oral administration of 75 grams of (g) glucose.

A "sample" refers to human whole blood, a blood fraction (plasma or serum), a cell, a tissue and a transformed cell line.

A "significant difference" refers to a change between OGTT readings that shows a subject has converted from IS to IR or the reverse (IR to IS) based on the IR index.

"Status" refers to the current diagnosis of a subject or patient as IS, IR or NIDDM.

DESCRIPTION OF THE INVENTION

IS, IR and NIDDM were diagnosed by stressing a subject's system with a defined glucose load and then measuring the concentrations of glucose, endogenous insulin, lipids and alanine aminotransferase (ALT) in subject samples taken over a 0-120 minute period. To satisfy required protocol, samples were taken from subjects in at least three different Beijing hospitals These subjects were between 30 and 65 years of age, had normal thyroid function, were not pregnant, had not been diagnosed with any liver, kidney, heat, or infectious disease, and had fasted overnight (~10-12 hours) prior to testing. Each subject was given an oral dose of 75 g glucose and blood samples were taken by venipuncture at 0, 60 and 120 minutes (min) after the administration of glucose. Data from subjects with ALT greater than 80 U/L, fasting glucose concentration greater than 126 mg/dl, or glucose concentration greater than 200 mg/dl at 120 minutes after administration of 75 g glucose were excluded from further study. In the present invention, all glucose concentrations were reported in mg/dl; insulin, in µIU/ml; triglyceride (TG), in mg/dl; high density lipoprotein (HDL) cholesterol, in mg/dl and ALT, in U/L. Total cholesterol and low density lipoprotein cholesterol concentrations and results of urinalysis were also recorded for each subject (data not shown).

All data were analyzed statistically. Mean and standard deviation were calculated for the OGTT glucose data from 1389 non-diabetic subjects by age and gender as shown in the table presented in Example II under Beijing Dataset. After being parsed into deciles, the Beijing dataset was compared with deciles for 490 subjects in a Stanford dataset (cf. Tuan et al.) characterized using SSPG. The comparison is summarized in the tables presented in Example II under Comparison of the Beijing and Stanford Datasets. Glucose concentrations were not found to be significantly different between the Beijing and Stanford datasets.

Subsequently, the data from the Beijing dataset were parsed into tertiles that became the reference populations for defining IS and IR. Distribution of all glucose and insulin concentrations in these populations were checked for normality, and endpoints and/or ranges of the population data were used to set diagnostic criteria and to define the IR index.

Exemplary data for IS and IR reference populations used in defining the IR index are shown in Figures (FIGS.) 1 and 2, respectively. The column headings for FIGS. 1 and 2 are: column one shows gender (M/F); column two, age; column three, glucose concentration at zero minutes (0'); column four, glucose concentration at sixty minutes (60'); column five, glucose con on at 120 minutes (120'); column six, insulin concentration at zero minutes (0'); column seven, insulin concentration at sixty minutes (60'); column eight, insulin concentration at 120 minutes (120'), column nine, TG concentration; column ten, HDL concentration; and column eleven, the TG/HDL ratio.

The IR index was validated by using it to identify IR and IS individuals in the Stanford dataset (490 individuals previously tested for IR using SSPG). Sensitivity and specificity were assessed for diagnosing both IS and IR, and the results are shown and summarized in Example III.

Utility of the IR Index

The invention presents a method for diagnosing IS, IR, and NIDDM using data from reference populations comprising administering 75 g glucose to the subject, obtaining a sample from the subject at 0, 60, and 120 min after glucose administration, performing OMIT, triglyceride and HDL tests on the subject sample, calculating a TG/HDL ratio, comparing glucose and insulin concentrations and TG/HDL ratio from the subject sample with endpoints and ranges from data from reference populations, wherein a first reference population that is diagnosed as IS has a glucose concentration at 0 min that is less tan 126 mg/dl, at 60 min that is less than or equal to 121 mg/dl and at 120 min is less than or equal to 100 mg/dl; an insulin concentration at 0 min that is less than or equal to 24 µIU/ml and at 60 min that is less than 50 µIU/ml or at 120 min that is less than 40 µIU/ml; and a TG/HDL ratio that is less than 2; a second reference population that is diagnosed as IR has a glucose concentration at 0 min that is less than 126 mg/dl, at 60 min that is equal to or greater than 170 mg/dl and at 120 min that is equal to or greater than 127 and less than 200 mg/dl and an insulin concentration at 0 min that is less than or equal to 55 µIU/ml and at 60 min or at 120 min that is greater than 60 µIU/ml; and a third reference potion that is diagnose as NIDDM and has a glucose concentration at 0 min that is equal to or greater than 126 mg/dl or at 120 min that is greater than 200 mg/dL; and diagnosing whether the subject is IS, IR or NIDDM based on the comparison.

The invention also presents use of an IR index to diagnose IS, IR and NIDDM based on 0, 60 and 120 min concentration ranges for glucose and insulin and fasting TG/HDL ratio from reference populations following 75 g glucose administration further comprising a diagnosis of IS if a subject has a glucose concentration at 0 min that is from about 50 mg/dl to about 125 mg/dl, at 60 min that is from about 62 mg/dl to about 121 mg/dl, and at 120 min that is from about 57 mg/dl to about 100 mg/dl; an insulin concentration at 0 min that is from about 1 µIU/ml to about 24 µIU/ml and at 60 min that is from about 17 µIU/ml to about 50 µIU/ml or at 120 min that is from about 3 µIU/ml to about 40 µIU/ml; and a TG/HDL ratio that is less than 2; a diagnosis of IR if a subject has a glucose concentration at 0 min from about 81 mg/dl to about 125 mg/dl, at 60 min from about 170 mg/dl to about 283 mg/dl, and at 120 min that is from about 127 to about 199 mg/dl; an insulin concentration at 0 min that is from about 4 µIU/ml to about 55 µIU/ml and at 60 min or at 120 min that is from about 60 µIU/ml to about 240 µIU/ml; and a diagnosis of NIDDM if the subject has a glucose concentration at 0 min that is greater than 126 mg/dl or at 120 min that is greater than 200 mg/dl.

The ability to diagnose subjects as IS or IR based on the IR index is novel in the art.

OGTT glucose and insulin, TG and HDL testing and the IR index are useful as part of an annual physical exam to screen a subject for IR months to years before physical symptoms show disease onset. Such screenings are particularly important for subjects with first degree relatives that have been diagnosed with IR, NIDDM or cardiovascular disease. The ability to diagnose IS or IR has many implications.

The first implication is t a subject who is tested diagnosed as IS, and has no first degree relatives that have been diagnosed with IR, NIDDM or cardiovascular disease is less likely to have age-related diseases and disorder.

The second implication is that a subject who is tested and diagnose as IR is considered to be pre-diabetic. If the subject has a first degree relative (parent or sibling) who has been diagnosed with IR or NIDDM, the subject is genetically "at risk", predispose or susceptible, to developing IR-related conditions and NIDDM. IR-related conditions include, but are not limited to, dyslipidemia, hypoglycemia, hyperinsulinemia, metabolic syndrome, nonalcoholic fatty liver disease, polycystic ovary some, prediabetes, sleep apnea, syndrome x cardiovascular diseases such as athecsciersois, peripheral vascular disease, myocardial infraction and stroke; and cancers such as ba, colorectal and prostate cancers.

The diagnosis of IR is both a warning and a opportunity to affect lifestyle changes or seek medical intervention to delay the onset or ameliorate the severity of IR-Mated or conversion to NIDDM. The subject can consult with a doctor or clinic to institute an exercise program and to be apprised of drugs that moderate high blood pressure, high cholesterol, high density lipoprotein, low density lipoprotein and obesity.

The third implication is that an IS subject with first degree relatives with IR or NIDDM or an IR subject can be retested at regular intervals. An IS subject should be retested at least once every three years, an IR subject, about once a year to monitor status. It is contemplated that an IS diagnosis can become an IR diagnosis, or the reverse, based on age, genetics, lifestyle and medical intervention.

Similarly, the ability to diagnose NIDDM as early as possible allows the subject and doctor or clinic to monitor progression of NIDDM and the onset of NIDDM-associated conditions. NIDDM and NIDDM-associated conditions are correlated with a higher mortality and morbidity and include, but are not limited to, IR-related conditions, neurological diseases and disorders such as cerebrovascular disease, ischemic and hemorrhagic stroke, neuralgia, neropathy, and transient ischemic attacks; pressure vascular diseases such as atheroschlerosis, chronic foot ulcers, gangrene and thrombosis; cardiovascular diseases such as aneurysms, angina, cardiac dysrhythmias, cardiomyopathy, hypertension, ischemic heart disease and myocardial infarction; diabetic renal disease such as nephropathy, proteinuria, and renal failure; endocrine/metabolic complications, opthalmic complications including cataract, glaucoma, and blindness; and compromised response to bacterial and fungal infections.

An IR Calculator

Figure 3A:
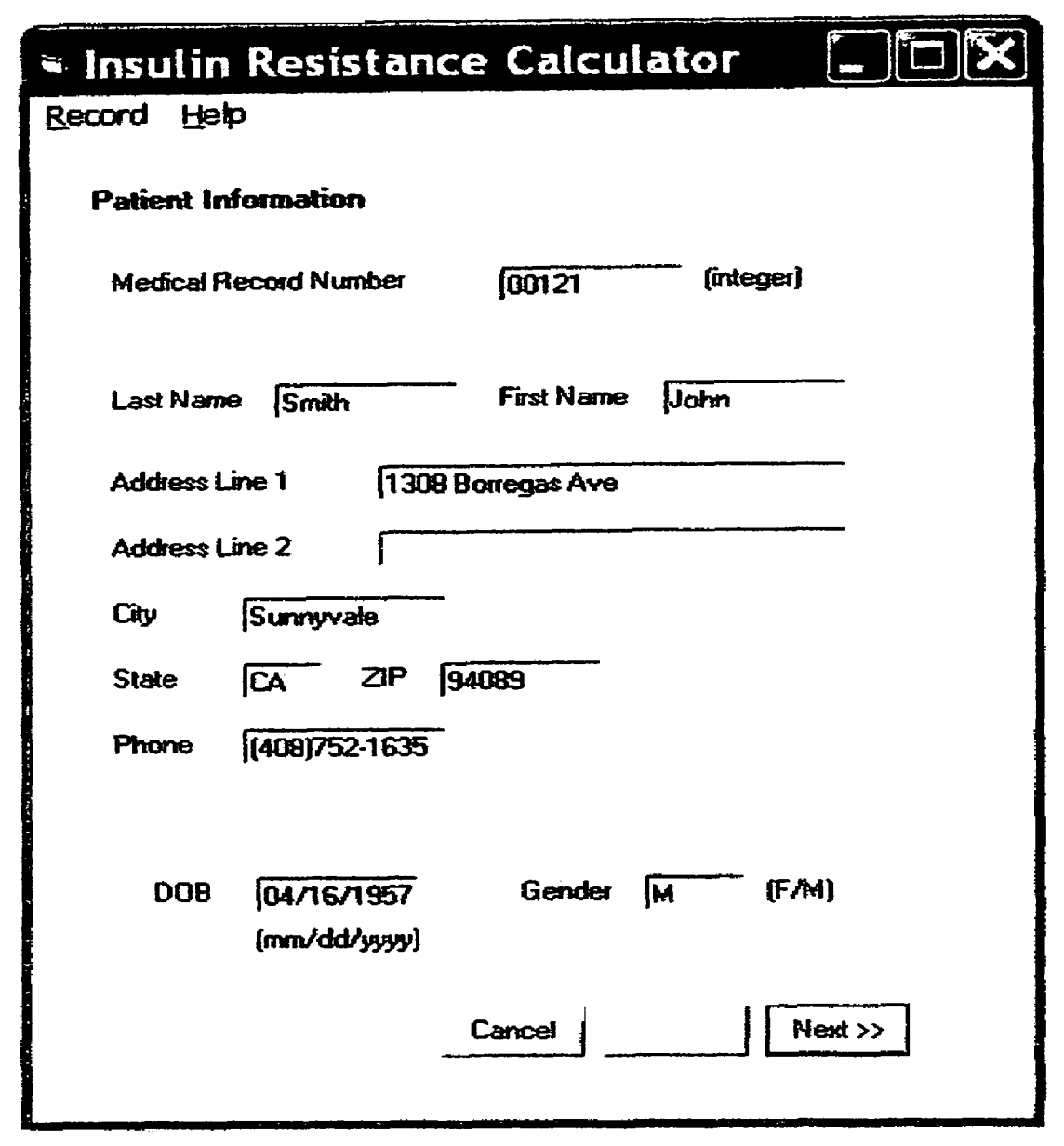

The invention also presents an IR calculator that can be used in a doctor's office, clinic or laboratory. A technician can enter ALT, OGTT readings and lipid concentrations into the IR calculator or a simple script can be written to import results in batch mode. Either way, the IR calculator compares the OGTT readings and TG/HDL ratio to the IR index and provides a status report Based on comparison of the test results to the IR index, a patient (hereinafter used in all sections and claims that refer to use of the IR calculator) can be diagnosed as IS, IR, or NIDDM. The patient records can be stored in a clinic, hospital, regional or national medical database, downloaded onto devices used by medical practitioners, or printed for the patient's file or to be given or sent to the patient The IR calculator is shown in FIGS. 3A-3C, and its operation is described in Example IV.

It is to be understood that the invention is not limited to the particular methodology, protocols, and reagents described, as these may vary. It is also understood that the terminology used herein is for the purpose of describing particular embodiments only and is not intended to limit the scope of the present invention. The examples below are provided to enable and illustrate the subject invention and are not included for the purpose of limiting the invention.

EXAMPLES

I Measuring Glucose, Insulin and Lipids

An OGTT was performed on 1389 unrelated, non-diabetic subject. All subjects had normal thyroid function and were not known to be pregnant or affected by any liver, kidney, heart, or infectious disease. Individuals who were diagnosed as diabetic (having a glucose concentration greater Oman 126 mg/dl at 0 min or greater than 200 mg/dl at 120 min after glucose administration) or had triglyceride over 600 mg/dl, total cholesterol greater than 600 mg/dl, systolic blood pressure greater fan 170 mmHg, diastolic blood pressure greater than 100 mmHg or BMI greater than 32 kg/m$^2$ or less than 18 kg/m$^2$, were excluded After an overnight fast of 10-12 hours, subjects reported to the hospital and were given 75 g glucose orally (83 g prepared sugar powder containing 75 g D glucose in 12 ounces of water, LongFu Hospital, Beijing, China). Five ml of blood were collected by venipuncture at 0, 60 and 120 min after the administration of glucose and placed in sterile test tubes (without anticoagulated). After coagulation, serum from each subject was aliquoted for determination of glucose, insulin, lipid and ALT concentrations. This study was IRB-approved, and the informed consent of all subjects was obtained prior to testing.

Measurements of Glucose concentration

All glucose concentrations were analyzed using the standard hexokinase method and Olympus AU2700 Chemistry-Immuno analyzer (Olympus America, Melville N.Y.). All procedures were performed according to manufacture's instructions. To ensure the quality and consistency of the data, the analyzer was calibrated twice a week using standards with known glucose concentrations.

Measurements of Insulin Concentration

All insulin concentrations were analyzed using COAT-A-COUNTS® Insulin Radioimmunoassay kits (Diagnostic Products, Los Angeles Calif.). In this solid-phase radioimmunoassay, $^{125}$I-labeled insulin competes with insulin in the sample for sites on an insulin-specific antibody. All procedures were performed for the fixed time period specified by the manufacturer.

Briefly, 200 µl of serum collected from each subject at each time point was mixed with 1.0 ml of $^{125}$I-insulin (tracer) in a COAT-A-COUNT® tube (Diagnostic Products) pre-coated with fixed amount of insulin-specific antibody. After 18-24 hours incubation at room temperature, the supernatant was decanted; and the tube was allowed to drain for 2-3 minutes. The radioactivity in the tube was counted for one minute using an SN-697, automatic gamma radiation counter (Shangha He-Suo-Ri-Huan Photoelectric Instrument Ltd., Shanghai, China). Counts were converted to insulin concentration in µIU/ml according to the manufacturer's instructions. To ensure data quality and consistency, duplicate sample aliquots were tested against standards and controls provided in the test kit by the manufacture.

Measurements of Lipid Concentration

Fasting HDL level was measured in serum using the Direct HD-cholesterol kit (Zhongsheng Beijing Bio-Technology and Science, Beijing China) according to the manufactuer's instructions or a Roche/Hitachi Automatic Clinical Analyzer system (Roche Diagnostics, Basel, Switzerland).

Fasting TG con was measured in serum using the GPO-PAP enzymatic method according to the manufacture's instructions (Zhongsheng Beijing Bio-Technology and Science, Beijing China).

In the alternative. TG and HDL levels can be measured using diagnostic kits commercially available from Wako Chemicals USA (1600 Bellwood Road, Richmond Va.).

TG/HDL ratio was calculated for all 0 min subject samples.

II Analysis and Defining the IR Index

Beijing Dataset

OGTT data for 1389 non-diabetic Beijing subjects were analyzed using standard statistical program software (version 10.1; SSPS Inc, Chicago Ill.) Glucose concentrations were recorded for each of the time points, and mean and standard deviation were cat for each time point as shown below. Column one shows age distribution, column two, gender; column three, number of subjects (No.); and columns four-nine, the mean and standard deviations for OGTT glucose concentrations at 0 min, 60 min and 120 min. respectively. As was en these data show that the ability to metabolize glucose decreases, and the mean concentration of glucose in the blood increases with age, particularity in females.

| Age | Gender | No. | OGTT Glucose | | | | | |
|---|---|---|---|---|---|---|---|---|
| | | | 0' | | 60' | | 120' | |
| | | | Mean | STDEV | Mean | STDEV | Mean | STDEV |
| <30 | F | 34 | 83 | 9 | 107 | 38 | 92 | 22 |
| | M | 20 | 88 | 7 | 128 | 25 | 99 | 21 |
| 30-39 | F | 191 | 89 | 9 | 122 | 39 | 105 | 23 |
| | M | 124 | 92 | 10 | 151 | 49 | 112 | 32 |
| 40-49 | F | 341 | 92 | 9 | 136 | 44 | 114 | 26 |
| | M | 158 | 93 | 10 | 156 | 50 | 111 | 32 |
| 50-59 | F | 290 | 93 | 10 | 145 | 45 | 119 | 29 |
| | M | 128 | 95 | 10 | 165 | 47 | 115 | 30 |
| 60+ | F | 71 | 98 | 9 | 170 | 45 | 138 | 32 |
| | M | 32 | 94 | 11 | 153 | 51 | 112 | 32 |
| All | F | 927 | 92 | 10 | 137 | 45 | 115 | 28 |
| | M | 462 | 93 | 10 | 156 | 49 | 112 | 31 |

Comparison of the Beijing and Stanford Datasets

OGTT glucose data from the Beijing t and SSPG data from the Stanford dataset were parsed into deciles for comparison. The Stanford dataset contained the SSPG data from 490 subjects of mixed ethnicity (77% Caucasion, 12% Asian, 10% Hispanic amd 1% Black) and with ages ranging from 19-79 years as shown below. Column one shows summmay labels—number of subjects (No.), mean and standard deviation (STDEV)l column two, deciled; column three, SSPG (mg/dl) at 0 min; column four, SSPG (mg/dl) at 60 min; and column five, SSPG (mg/dl) at 120 min.

| Deciles | SSPG 0' | SSPG 60' | SSPG 120' |
|---|---|---|---|
| 10 | 77 | 89 | 70 |
| 20 | 81 | 105 | 81 |
| 30 | 85 | 119 | 89 |
| 40 | 88 | 129 | 96 |
| 50 | 91 | 138 | 103 |
| 60 | 93 | 146 | 111 |
| 70 | 96 | 162 | 121 |
| 80 | 100 | 175 | 130 |
| 90 | 106 | 190 | 151 |
| Summary: | | | |
| No. | 490 | 490 | 490 |
| Mean | 91.1 | 140.4 | 107.4 |
| STDEV | 11.4 | 40.4 | 30.8 |

The Beijing dataset, with OGTT glucose (mg/dl) parsed into deciles is shown below. Column one shows summary labels—number of subjects (No.), mean and standard deviation (STDEV); column two, deciles; column three, OGTT (mg/dl) at 0 min; column four, OGTT (mg/dl) at 60 min; and column five, OGTT (mg/dl) at 120 min.

| Deciles | OGTT 0' | OGTT 60' | OGTT 120' |
|---|---|---|---|
| 10 | 81 | 87 | 80 |
| 20 | 84 | 101 | 90 |
| 30 | 87 | 114 | 97 |
| 40 | 89 | 126 | 103 |
| 50 | 91 | 137 | 110 |
| 60 | 94 | 150 | 117 |

-continued

| Deciles | OGTT 0' | OGTT 60' | OGTT 120' |
|---|---|---|---|
| 70 | 96 | 165 | 125 |
| 80 | 100 | 184 | 136 |
| 90 | 105 | 208 | 154 |
| Summary: | | | |
| No. | 1389 | 1388 | 1389 |
| Mean | 92.3 | 143.5 | 113.7 |
| STDEV | 9.7 | 47.0 | 29.2 |

As shown above, the Stanford and Being d s were not found to be significantly different in glucose concentration. Some of the mean values for the Beijing dataset based on OGTT were slightly higher than those for the Stanford dataset based on SSPG.

Defining the IR Index

The Beijing OGTT data at 0 min, 60 min and 120 min was parsed into tertiles and the ranges and endpoints of data from the reference populations were used in defining the IR index. The IR index is presented in the table and paragraphs below. Column one shows the biomarkers, column two, the timepoints in minutes; column three the contraction ranges for IS; column four, the concentrations ranges for IR; and column 5, the endpoints for NIDDM.

| Biomarkers | Min | IS | IR | NIDDM |
|---|---|---|---|---|
| OGTT glucose (mg/dl) | 0 | ≧50 and <126 | ≧81 and <126 | ≧126 |
| OGTT glucose (mg/dl) | 60 | ≧62 and ≦121 | ≧170 and ≦283 | |
| OGTT glucose (mg/dl) | 120 | ≧57 and ≦100 | ≧127 and ≦199 | ≧200 |
| OGTT insulin (µIU/ml) | 60 | ≧17 and <50 | >60 and ≦240 | |
| OGTT insulin (µIU/ml) | 120 | ≧3 and <40 | >60 and ≦240 | |
| TG/HDL Ratio | | <2 | | |

Insulin Sensitive

A subject is identified as IS using the IR index if the subject has a glucose concentration at 0 min that is from about 50 mg/dl to about 125 mg/dl, at 60 min that is from about 62 mg/dl to about 121 mg/dl and at 120 min that is from about 57 mg/dl to about 100 mg/dl; an insulin concentration at 0 min that is from about 1 µIU/ml to about 24 µIU/mL at 60 min that is from about 17 µIU/ml to about 50 µIU/ml or at 120 min that from about 3 µIU/ml to about 40 µIU/ml; and a fasting TG/HDL ratio that is less than 2.

Insulin Resistant

A subject is identified as IR using the IR index if the subject has a glucose concentration at 0 min from about 81 mg/dl to about 125 mg/dl, at 60 min from about 170 mg/dl to about 283 mg/dl, and at 120 min that is from about 127 to about 199 mg/dl; an insulin on at 0 mn that is from about 4 µIU/ml to about 55 µIU/ml, and at either 60 min or at 120 min that is from about 60 µIU/ml to about 240 µIU/ml.

NIDDM

A subject is diagnosed as NIDDM using the IR index if the subject has a glucose concentration at 0 min that is equal to or greater than 126 mg/dl or at 120 min that is equal to or greater than 200 mg/dl.

III Validation of the IR Index

The ability of the IR index to correctly identify IS or IR subjects was tested against the Stanford dataset. Within the Stanford dataset a group of 389 subjects between the ages of 30 and 65, the same age range as the Beijing dataset, were diagnosed as non-diabetic using SSPG. Stanford subjects were classified as IS, if the subject had a SSPG concentration of less than 83 mg/dL; IRK if the subject had a SSPG concentration of more than 212 mg/dL; non-IS/non-IR if the subject had a SSPG concentration between 83 and 212 mg/dl. OGTT and lipid tests were also performed on samples in the Stanford dataset (data not shown).

The IR index was applied to 389 non-diabetic subjects Insulin sensitive subjects identified using the IR index were labeled as IS predicted (ISp) and compared with the IS diagnostics based on SSPG. Similarly, insulin resistant subjects identified using the IR index were labeled as IR predicted (IRp) and compared to the IR diagnosis based on SSPG. Using diagnosis by SSPG as the gold stand, the specificity and sensitivity of the IR index were evaluate Both "sensitivity", the proportion of truly IS or IR persons as measured by SSPG who were correctly identified as IS or IR using the IR index, and "specificity", the proportion of non-IS or non-IR subjects as measured by SSPG who were correctly identified as non-IS or non-IR using the IR index were calculated. The tables below summary the specificity and sensitivity for prediction of IS and IR, respectively. Column one in the first table provides labels for the rows of the table—SSPG ranges in mg/dl; insulin sensitive subjects identified using the IR index (ISp), by number (No.) and percent (%); and Total subjects, by No. and %. Colunn two shows IS statistics; column thee, non-IS/non-IR statistics; cohnnn four, IR statistics; colunn five, Total; column six, specificity (%); and column seven, sensitivity (%).

| | | IS | non-IS/non-IR | IR | Total | Specificity | Sensitivity |
|---|---|---|---|---|---|---|---|
| SSPG(mg/dl) | | <83 | 83-212 | >212 | | 90.24% | 33.33% |
| IS p | No. | 34 | 25 | 3 | 62 | | |
| | % | 54.8 | 40.3 | 4.8 | 100 | | |
| Total | No. | 102 | 187 | 100 | 389 | | |
| | % | 26.2 | 48. | 25.7 | 100 | | |

Column one in the second table provides labels for the rows of the table—SSPG ranges in mg/dl; insulin resistant subjects identified using the IR index (IRp), by number (No.) and percent (%); and Total subjects, by No. and %. Column two shows IS statistics; column tree, non-IS/non-IR statistics; column four, IR statistics; column five, Total; column six, specificity (%); and column seven, sensitivity (%)

| | | IS | non-IS/non-IR | IR | Total | Specificity | Sensitivity |
|---|---|---|---|---|---|---|---|
| SSPG(mg/dl) | | <83 | 83-212 | >212 | | 93.08% | 31.00% |
| IR p | No. | 1 | 19 | 31 | 51 | | |
| | % | 2 | 37.2 | 60.8 | 100 | | |
| Total | No. | 102 | 187 | 100 | 389 | | |
| | % | 26.2 | 48 | 25.7 | 100 | | |

The specificity and sensitivity of using the IR index to identify both IS and IR subjects were found to be acceptable.

The differences between diagnosis of IS and IR using SSPG and the IR index can be attributed to the following: 1) OGTT measures circulating glucose/insulin levels and reflects whole body glucose metabolism as influenced by multiple organs and tissues including the liver, pancreas, and adipose tissue, and 2) differences in diet, genetics, and lifestyle of an Asian versus primarily Caucasian population.

IV IR Calculator and Record Generation

Insulin Resistance Calculator

An IR calculator was developed to automate screening and diagnosis of IS, IR and NIDDM based on the IR index. The IR calculator was created using he Visual Basic 6.0 (Microsoft Corp, Redmond Wash.), can be distributed to clients on a CD or made accessible on the world-wide-web, and can generate electronic and/or paper records.

The steps for running the IR calculator are: 1) Start the application/program, 2) Fill in patient information, 3) Fill in glucose, insulin, TG, HDL and ALT concentrations, and 4) click the button labeled "Calculate". The IR calculator report shows IS or IR status based on OGTT glucose and insulin concentrations and TG/HDL ratio. The standards for IS and IR are listed, and previous records for the patient (if any were stored in the database) are available at the bottom of the report. Once the report is generated, the technician or person operating the IR calculator can click the button for: a) "Save Record" (into the hospital or clinic database), b) "Print report" (to be placed in the patient's medical folder or given/mailed the subject), or c) "New Record" to start the process for the next patient.

Screenshots of the IR calculator are shown in FIG. 3. FIG. 3A shows the information to be entered into the first page of the IR calculator: medical identification number, first and last name, address, phone number, date of birth (DOB) and gender (M/F) of the patient FIG. 3B shows the 0', 60' and 120' windows into which OGTT readings for glucose and insulin and fasting TG, HDL and ALT readings are to be entered. FIG. 3C shows the IR calculator report, stats, standard, and test results. IS or IR status provides a diagnosis, a paragraph suggesting that a patient diagnosed as IR or NIDDM work with the doctor or clinic to control disease progression, and a suggested frequency for resting. The standards for determining IS and IR are listed for reference directly above the records for the patient's record(s) for ALT, TG/HDL and OGTT readings. Each test date will have available results listed as a line as the report.

Record Generation

The purpose of developing the IR calculator was to automate the comparison of patient readings to the IR index and to generate a record with the patient's current status. The patient's record, as stored in the clinic, hospital or regional database, contains both raw data—concentrations of glucose, insulin, TG and HDL —and results that can be downloaded into a hand-held device carried by a medical practitioner, or printed for inclusion in the patients chart or medical folder. Each record will contain medical identification number, the patient's name and address, and age; the date of the test and the current OGTT readings; the date of any previous tests and OGTT readings; the diagnosis and suggested frequency for retesting.

In addition, an individualized record can be printed The record will contain the date of the test; the patient's medical identification number, name, address, gender and age; the glucose, insulin, TG and HDL concentrations from the current and previous test results (if any are present in the base); ranges for determination of IS, IR, and NIDDM; a diagnosis and the suggested frequency for retesting If the patient is diagnosed as IS, retesting is suggested in about three years If the patient is diagnosed as IR, retesting is suggested in about one year.

For a patient diagnosed as IR, the individualized record may include any of the data above and the substance of the following advisory information (for IR, result shown in FIG. 3C): "You have been diagnosed as IR. This test of your ability to metabolize glucose has shown that you are at risk for developing type 2 diabetes and IR-related conditions. Please consult your doctor or clinic about the best treatment for you. You can affect disease progression by being a regular exercise program, following a healthy diet as recommended by the ADA, AHA, the clinic or your doctor, and/or by taking certain medicines to reduce risk factors such as high blood pressure, cholesterol and obesity".

For a patient diagnosed as NIDDM, the individualized record may include all of the data above and the substance of the following advisory information: "You have been diagnosed with type 2 diabetes (NIDDM). This test has shown that you have decreased ability to metabolize glucose and are at risk for NIDDM-associated conditions Please consult your doctor or clinic about the need for additional testing. You can affect disease progression by beg g a regular exercise program, following a healthy diet as recommended by the ADA, AHA, the clinic or your doctor, and/or taking certain medicines to reduce risk factors such as high blood pressure, cholesterol and obesity. If necessary, your doctor may prescribe the use of a glucose monitor, insulin and/or other medicines to regulate your blood sugar".

For both IR and NIDDM records, the wording of the advisory information should be considered exemplary as many different presentations of this information can be contemplated. In fact, it is contemplated that the IR calculator and records can be modified to suit particular customer needs. This would entail changing either input screens or windows or output screens or windows to include data desired by that customer. Such modifications are well known to those in the art who use scripts and/or programs to run analyses or produce subject patient records such as these described above.

All patents and publications mentioned in the specification are incorporated by reference herein. Various modifications and variations of the described methods and calculator of the invention will be apparent to those skilled in the art without departing from the scope and spirit of the invention. Although the invention has been described in connection with specific preferred embodiments, it should be understood that the invention as claimed should not-be unduly limited to such specific embodiments. Indeed, various modifications of the described modes for carrying out the invention that are obvious to those skilled in diagnostic field are intended to be within the scope of the following claims.

What is claimed is:

1. A method for diagnosing whether a subject is insulin sensitive (IS), insulin resistant (IR) or diabetic (NIDDM) comprising:
   a) administering 75 grams of glucose to the subject;
   b) obtaining samples from the subject at 0, 60 and 120 min after glucose administration;
   c) performing tests on the samples to obtain sample readings wherein the sample readings are concentrations of glucose, insulin, triglyceride (TG) and high density lipoprotein (HDL);

d) calculating TG/HDL ratio from the sample readings for TG and HDL;

e) comparing sample readings for glucose and insulin concentrations and TG/HDL ratio to readings from reference populations wherein i) a first reference population that has been diagnosed as IS has a glucose concentration at 0 min that is less than 126 mg/dl, at 60 min that is less than or equal to 121 mg/dl and at 120 min is less than or equal to 100 mg/dl; an insulin concentration at 0 min that is less than or equal to 19 µIU/ml, at 60 min that is less than 50 µIU/ml or at 120 min that is less than 40 µIU/ml; and a TG/HDL ratio that is less than 2;

ii) a second reference population that has been diagnosed as IR has a glucose concentration at 0 min that is less than 126 mg/dl, at 60 min that is equal to or greater than 170 mg/dl and at 120 min that is equal to or greater than 127 and less than 200 mg/dl and an insulin concentration at 0 min that is less than or equal to 55 µIU/ml and at 60 min or at 120 min that is greater than 60 µIU/ml; and iii) a third reference population that has been diagnosed as NIDDM has a glucose concentration at 0 min that is equal to or greater than 126 mg/dl or at 120 min that is greater than 200 mg/dl;

f) diagnosing whether the subject is IS, IR or NIDDM based on the comparison.

2. The method of claim 1 wherein the sample readings for glucose and insulin concentrations and TG/HDL ratio in the reference populations define an insulin resistance index (IR index) further comprising:

a) a diagnosis of IS if a subject has a glucose concentration at 0 min that is from about 50 mg/dl to about 125 mg/dl, at 60 min that is from about 62 mg/dl to about 121 mg/dl, and at 120 min that is from about 57 mg/dl to about 100 mg/dl; an insulin concentration at 0 min that is from about 1 µIU/ml to about 24 µIU/ml and at 60 min that is from about 17 µIU/ml to about 50 µIU/ml or at 120 min that is from about 3 µIU/ml to about 40 µIU/ml ; and a TG/HDL ratio that is less than 2;

b) a diagnosis of IR if a subject has a glucose concentration at 0 min from about 81 mg/dl to about 125 mg/dl, at 60 min from about 170 mg/dl to about 283 mg/dl, and at 120 min that is from about 127 to about 199 mg/dl; an insulin concentration at 0 min that is from about 4 µIU/ml to about 55 µIU/ml and at 60 min or at 120 min that is from about 60 µIU/ml to about 240 µIU/ml ; and c) a diagnosis of NIDDM if a subject has a glucose concentration at 0 min that is greater than 126 mg/dl or at 120, that is greater than 200 mg/dl.

3. The method of claim 2 wherein the diagnosis of IS or IR suggests a frequency for retesting.

4. The method of claim 3 wherein the frequency for retesting an IS subject is about once every three years.

5. The method of claim 3 wherein the frequency for retesting an IR subject is about once a year.

6. The method of claim 2 wherein an IS subject is retested further comprising:

a) administering 75 grams of glucose to the subject;
  b) obtaining samples from the subject at 0, 60 and 120 min after glucose administration;
  c) performing tests on the samples to obtain sample readings wherein the sample readings are concentrations of glucose, insulin, TG and HDL;
  d) calculating TG/HDL ratio from the sample readings for TG and HDL;
  e) comparing sample readings for glucose and insulin concentrations and TG/HDL ratio to the IR index; and
  f) diagnosing whether the subject is IS, IR or NIDDM based on the comparison.

7. The method of claim 2 wherein an IR subject is retested further comprising:

a) administering 75 grams of glucose to the subject;
  b) obtaining samples from the subject at 0, 60 and 120 min after glucose administration;
  c) performing tests on the samples to obtain sample readings wherein the sample readings are concentrations af glucose, insulin, TG and HDL;
  d) calculating TG/HDL ratio from the sample readings for TG and HDL;
  e) comparing sample readings for glucose and insulin concentration and TG/HDL ratio to the IR index; and
  f) diagnosing whether the sobject is IS, IR or NIDDM based on the comparison.

8. A method of claim 2 wherein a subject previously diagnosed as IS or IR is evaluated for disease progression further comprising:

a) administering 75 grams of glucose to the subject;
  b) obtaining samples from the subject at 0, 60 and 120 min after glucose administration;
  c) performing tests on the samples to obtain sample readings wherein the sample readings are concentrations of glucose, insulin, TG and HDL;
  d) calculating TG/HDL ratio from the sample readings for TG and HDL;
  e) comparing sample readings for glucose and insulin concentration and TG/HDL ratio to the IR index; and
  f) determining that increased sample reading concentrations causing a change in status from IS to IR or from IR to NIDDM indicates disease progression.

9. The method of claim 2 wherein the sample readings for glucose and insulin concentrations and TG/HDL ratio are compared to the IR index using an IR calculator.

10. The method of claim 9 wherein the IR calculator is loaded into a progammable device or is accessible on the world-wide-web.

11. The method of claim 9 wherein the IR calculator is used to automate comparisons in batch mode.

12. The method of claim 9, wherein the IR calculator is used to generate a patient record containing medical record number, name, address, date of birth, gender, date of test, glucose concentrations, insulin concentrations, TG/HDL ratio, alanine aminotransferase (ALT), IS, IR or NIDDM status, standard ranges defining IS, IR and NIDDM, and frequency for retesting.

13. The method of claim 12 wherein previous sample readings for the patient found in a database are listed by date in the record.

14. The method of claim 12 wherein IR or NIDDM status suggests lifestyle change and/or medical intervention.

* * * * *